United States Patent [19]

Welch

[11] Patent Number: 4,607,022

[45] Date of Patent: Aug. 19, 1986

[54] OLEFIN CONVERSION CATALYST

[75] Inventor: Bruce M. Welch, Bartlesville, Okla.

[73] Assignee: Phillips Petroleum Company, Bartlesville, Okla.

[21] Appl. No.: 733,837

[22] Filed: May 14, 1985

Related U.S. Application Data

[62] Division of Ser. No. 580,591, Feb. 16, 1984, Pat. No. 4,547,617.

[51] Int. Cl.[4] .......................... B01J 21/06; B01J 23/28
[52] U.S. Cl. ........................................ 502/242; 502/255
[58] Field of Search ................... 502/239, 242, 255; 585/646

[56] References Cited

U.S. PATENT DOCUMENTS

| | | | |
|---|---|---|---|
| 2,437,531 | 3/1948 | Huffman | 502/255 X |
| 3,261,879 | 7/1966 | Banks | 260/683 |
| 3,418,390 | 12/1968 | Heckelsberg | 260/683 |
| 3,792,106 | 2/1974 | Regler | 260/683 |
| 4,218,345 | 8/1980 | Hoff et al. | 502/255 X |
| 4,296,001 | 10/1981 | Hawley | 502/239 |
| 4,489,172 | 12/1984 | McDaniel | 502/239 |

*Primary Examiner*—Carl F. Dees
*Attorney, Agent, or Firm*—M. A. Montgomery

[57] ABSTRACT

Olefins are converted into other olefins having different numbers of carbon atoms by contact with a catalyst comprising a silica support containing molybdenum oxide and a promoting amount of a least one titaniferous agent and activated under conditions suitable for the titaniferous agent to promote the activity of molybdenum oxide and silica for the disproportionation and isomerization reaction.

11 Claims, No Drawings

OLEFIN CONVERSION CATALYST

This application is a divisional of application Ser. No. 580,591, filed 2/16/84, now U.S. Pat. No. 4,547,617.

BACKGROUND OF THE INVENTION

This invention relates to the conversion of olefins according to the olefin reaction, to catalysts therefore and to a method for modifying the activity of such catalysts. In accordance with one aspect, this invention relates to a catalyst comprising molybdenum, silica and at least one titaniferous agent or component suitable for use in the disproportionation and isomerization of olefins.

In accordance with another aspect, this invention relates to a catalyst suitable for use in the disproportionation and isomerization of olefins comprising silica and molybdenum promoted with at least one titaniferous agent or component.

In accordance with another aspect, this invention relates to a process for the disproportionation and isomerization of olefinic hydrocarbons with a disproportionation catalyst modified as hereinbefore described under conditions of temperature and pressure which effect disproportionation and isomerization of olefinic hydrocarbon feeds.

The disproportionation or metathesis of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene, and cis-, and trans-2-butene.

Another type of disproportionation involves the cross-disproportionation of two different olefins to form still other olefins. An example would be the reaction of one molecule of 2-butene with one molecule of 3-hexene to produce two molecules of 2-pentene.

By the term "disproportionation" or "metathesis" throughout the specification is meant the conversion of the feed olefinic (or unsaturated) hydrocarbon to a mixture of olefinic (or unsaturated) hydrocarbons having different numbers of carbon atoms than the feed hydrocarbons.

Among the catalysts that have been developed for disproportionation are those comprising silica containing a catalytic amount of molybdenum oxide. The present invention is based upon the discovery of a way to improve the activity of such a catalyst for the isomerization of olefins.

Previously it has been found that the activity of olefin reaction catalysts, e.g. disproportionation or metathesis catalysts, can be modified by admixture with a double bond isomerization catalyst. For example, mixtures of olefin reaction catalysts with magnesium oxide or zinc oxide are particularly effective in increasing conversion and/or widening the spread of products.

It has now been found that the isomerization activity of an olefin reaction catalyst, i.e. a disproportionation or metathesis catalyst, can be modified by treating the catalyst with a titaniferous agent.

Accordingly, an object of this invention is to provide a method for the conversion of olefins.

Another object of this invention is to provide a catalyst for the conversion of olefins.

Still another object of this invention is to provide a method for converting olefins to olefins having different numbers of carbon atoms from the feed hydrocarbons.

Still another object of this invention is to provide a method for modifying the activity of a disproportionation catalyst for the isomerization of olefins.

Other aspects, objects, and the several advantages of the invention will be apparent to one skilled in the art upon reading the disclosure including a detailed description of the invention and the appended claims.

SUMMARY OF INVENTION

In accordance with the present invention, a disproportionation (metathesis) catalyst comprising silica containing a catalytically effective amount of molybdenum is improved with respect to isomerization activity by contacting the catalyst with a promoting amount of at least one titaniferous agent or component under conditions suitable for the titaniferous agent to promote the isomerization activity of the molybdenum-silica catalyst.

Further, in accordance with a specific embodiment of the present invention, a disproportionation (metathesis) catalyst comprising silica containing a catalytically effective amount of molybdenum is modified by incorporating a promoting amount of least one titaniferous compound and then activating by heating under calcination and, optionally, reducing conditions suitable for the titaniferous compound to promote the isomerization activity of the molybdenum-silica catalyst.

Also according to the invention, a process is provided for the disproportionation and isomerization of an olefinic hydrocarbon by contacting the same with a disproportionation catalyst modified as hereinbefore described under conditions of temperature and pressure which effect disproportionation and isomerization of the feed.

DESCRIPTION OF SPECIFIC EMBODIMENTS

The silica component of the catalyst can be any conventional catalyst-grade silica. Some examples are: precipitated silica gel, microspheroidal silica, flame hydrolyzed silica, and silica aero-gels. These materials have appreciable suface area, usually in the range of 50–700 $m^2$ per g and can range from fine powders to course granules. These materials often contain small amounts of compounds of aluminum and of sodium in the order of a few tenths of a percent by weight and smaller. Trace amounts of other metals and such small amounts of these materials are acceptable.

The molybdenum component of the catalyst of the invention can be incorporated into the silica support by any suitable method including, for example, impregnation, dry mixing, and coprecipitation. Molybdenum oxide can be added directly or in the form of a molybdenum compound that can be converted to the oxide by calcination.

Generally the finished catalyst contains from about 0.1 to about 30 percent by weight of the molybdenum component calculated as the metal oxide and based on the total weight of the molybdenum component and the silica component, although larger amounts can be used. In most instances a proper amount of the promoter is from about 1 to about 20 percent. Excellent results have been obtained with silica-based catalysts containing from about 2 to about 15 percent by weight of molybdenum oxide.

The solid component of the catalyst can be in any conventional catalytic shape or size depending upon the type of conversion in which it is to be utilized. For example, in fixed-bed catalyst systems the solid composite can be in the form of spheres, pellets, extrudates, agglomerates, and the like. In slurry-catalyst systems, the solid can be in the form of relatively small particles or in the form of a powder.

According to the invention, a molybdenum-silica olefin reaction catalyst is modified by the inclusion of a titaniferous compound deposited on the surface thereof. The titaniferous compound is deposited on the surface of the catalyst by impregnation, coprecipitation, or other suitable means. The titaniferous compound can be incorporated as titanium (IV) oxide or as a compound convertible to titanium (IV) oxide by calcination. The titaniferous compound can be incorporated before, at the same time, or after the incorporation of the molybdenum compound into the silica support.

Representative examples of suitable titaniferous compounds (containing or yielding titanium) that can be used include:

Representative examples of suitable titaniferous compounds (containing or yielding titanium) that can be used include:

Titanium(IV)oxide;

Titanium alkoxides of the general formula Ti(OR)$_4$, where R is isopropoxide, titanium(IV)ethoxide, titanium(IV)n-butoxide, titanium(IV)2-ethylhexoxide;

Titanium carboxylates such as titanium(IV)oxalate, titanium(IV)citrate, titanium(IV)cresylate;

Titanium acetylacetonate; e.g., triethanolamine titanate, triethanolamine titanate chelate having the formula Ti(C$_3$H$_7$O)$_2$[OC$_2$H$_4$N(C$_2$H$_4$OH)$_2$]$_2$. (This is available from DuPont under the designation Tyzor TE);

Titanium halides, such as titanium(III)chloride, and titanium(IV)chloride, and the like, and mixtures thereof.

Generally, the finished catalyst contains from about 0.1 to about 20, preferably from about 1 to about 10 weight percent of the titanium component calculated as titanium dioxide and based on the total weight of the molybdenum oxide and the silica support.

To be effective in the present catalyst system, the above described components of the catalysts are activated at elevated temperatures, generally in flowing air. The activation or calcination of the catalyst is accomplished at a temperature of from about 300° C. to about 800° C. for a period of about several minutes to several hours or longer. A convenient and economical treatment is a temperature in the range of about 400°-700° C. for 0.5 to about 20 hours or longer.

The calcined catalyst described above can be, if desired, further subjected to a high temperature treatment in a reducing atmosphere. The temperature range and temperature of contact can be the same as used for calcination with a treating gas such as carbon monoxide, hydrogen, and the like. The activated catalyst is preferably cooled with an inert gas such as nitrogen prior to use in the olefin reaction.

The promoted catalyst can be used in disproportionation reactions in a conventional manner. The reaction temperature can vary depending upon the catalyst and feed(s) employed, but will be sufficient to effect disproportionation. Typically, the disproportionation is carried out at a temperature in the range of about 20° to about 600° C.

The disproportionation reaction can be carried out by contacting the olefins to be disproportionated with the catalyst in the liquid phase or the gas phase, depending on structure and molecular weight of the olefins, temperature and pressure.

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3-30 carbon atoms per molecule and with such cyclic olefins having 4-30 carbon atoms per molecule. Nontertiary olefins are those olefins wherein each carbon atom, which is attached to another carbon atom by means of a double bond, is also attached to at least one hydrogen atom. Internal olefins are preferred.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexene, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene, 6-methyl-6-ethylcyclooctadiene-1,4, and the like, and mixtures thereof.

The pressure during the disproportionation reaction may vary between wide limits. Pressures between 0.1 and 500 atm. are suitable; preferred pressures are between 0.5 and 250 atm. If possible, the process should be operated at a pressure which is atmospheric or nearly atmospheric so that no vacuum or pressure apparatus is required.

If the reaction is carried out in the liquid phase, solvents or diluents for the reactants may be used. Aliphatic saturated hydrocarbons (e.g., pentane, hexane, cyclohexane, dodecane) and aromatic hydrocarbons such as benzene and toluene are suitable. If the reaction is carried out in the gaseous phase, diluents such as aliphatic hydrocarbons (e.g., methane, ethane) and/or inert gases (e.g., nitrogen, argon) can be present. Preferably the disproportionation reaction is effected in the substantial absence of reactive materials such as water and oxygen.

The length of time during which the olefinically unsaturated compounds to be disproportionated are contacted with the catalyst depends upon several factors such as the activity of the catalyst, temperature, pressure, and structure of the olefinically unsaturated compound to be disproportionated. Contact time can conveniently vary between 0.1 second and 24 hours, although longer and shorter contact times may be used. The contact time needed to obtain a reasonable yield of disproportionated products depends on the factors mentioned above.

The process of the invention is effected batchwise or continuously, with fixed catalyst beds, slurried catalysts, fluidized beds or by using any other conventional contacting technique. The solid disproportionation catalysts are employed in any appropriate form, for example, as powders, flakes, pellets, spheres or extrudates.

The olefinic products of the invention, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

The following example illustrates the invention.

EXAMPLE

Catalyst preparation, activation and comparative disproportionation tests.

A macroporous, low sodium, low alumina silica base, having about 0.5 wt% $Na_2O$ and about 0.5 wt% $Al_2O_3$ and a surface area of 343 m²/g, formed into ⅛″ pellets was impregnated with aqueous ammonium molybdate. After drying in air at 250° C. for 1 hr. the catalyst contained about 10 wt% molybdenum oxide. This is designated catalyst 1, $MoO_3/SiO_2$ control catalyst.

A like portion of the above-described silica base was impregnated with an aqueous solution of bis(triethanolamine)titanium diisopropoxide (Tyzor TE, a product of E. I. du Pont de Nemours & Co., Inc. Wilmington, DE). The impregnated pellets were dried at 400° C. for 1 hr. After cooling the pellets were impregnated with aqueous ammonium molybdate. After drying in air at 250° C. for 1 hr, the catalyst contained about 10 wt% molybdenum oxide and 6.7% titanium dioxide. This is designated catalyst 2, $MoO_3/TiO_2/SiO_2$, the inventive catalyst.

A fixed bed of catalyst was formed in a vertical stainless steel tube reactor, ⅜″ o.d.×14″ long. Glass wool and glass beads were used to position the bed in the middle of the tube which was positioned in an electric tube furnace. The catalyst was activated by heating the bed at 550° C. in flowing air for 2 hr. then in CO for 30 min and cooling under argon flow at 160° C.

The reaction feed was 1-hexene purified by pumping it through beds of silica gel and MgO prior to entering the heated reactor. 1-Hexene was disproportionated in comparative runs over catalysts 1 and 2. In each six-hour run the reaction temperature was increased at one hour intervals. The pressure in the reactor was 50 psig. The results are presented in the following table.

TABLE 1

| Catalyst | Temp. (°C.) | WHSV* | 1-Hexene Conv., % | Selectivity to $C_{10}$ olefin, % | Liquid Product Distribution (mole %) | | | | | | | |
|---|---|---|---|---|---|---|---|---|---|---|---|---|
| | | | | | $C_5^=$ | $C_6^=$ (% 2-$C_6^=$) | $C_7^=$ | $C_8^=$ | $C_9^=$ | $C_{10}^=$ | $C_{11}^=$ | $C_{12}^=$ |
| 1 $MoO/SiO_2$ | 299 | 40 | 28.2 | 18.8 | 4.9 | 71.8(18.8) | 6.5 | 3.1 | 3.8 | 5.3 | 1.2 | 0.4 |
| 2 $TiO_2/MoO_3/SiO_2$ | 302 | 40 | 42.0 | 16.7 | 7.1 | 58.0(35.0) | 10.1 | 5.1 | 6.1 | 7.0 | 1.8 | 0.6 |
| 1 $MoO_3/SiO_2$ | 348 | 39 | 34.6 | 16.5 | 5.7 | 65.4(31.6) | 8.0 | 4.2 | 5.0 | 5.7 | 1.5 | 0.6 |
| 2 $TiO_2/MoO_3/SiO_2$ | 350 | 40 | 34.1 | 12.0 | 6.2 | 65.9(48.8) | 8.7 | 4.7 | 4.8 | 4.1 | 1.1 | 0.5 |
| 1 $MoO_3/SiO_2$ | 353 | 81 | 10.5 | 20.8 | 1.9 | 89.5(20.5) | 2.5 | 1.0 | 1.5 | 2.2 | 0.2 | 0.1 |
| 2 $TiO_2/MoO_3/SiO_2$ | 351 | 80 | 19.4 | 15.3 | 3.5 | 80.7(37.2) | 5.0 | 2.2 | 2.9 | 3.0 | 0.5 | 0.2 |
| 1 $MoO_3/SiO_2$ | 397 | 42 | 12.3 | 17.5 | 2.3 | 87.7(43.5) | 3.2 | 1.4 | 2.0 | 2.1 | 0.2 | 0.1 |
| 2 $TiO_2/MoO_3/SiO_2$ | 402 | 39 | 20.2 | 13.3 | 3.7 | 79.8(53.7) | 5.4 | 2.5 | 3.1 | 2.7 | 0.4 | 0.2 |
| 1 $MoO_3/SiO_2$ | 402 | 79 | 3.0 | 27.9 | 0.5 | 97.0(23.4) | 0.7 | 0.2 | 0.4 | 0.8 | — | — |
| 2 $TiO_2/MoO_3/SiO_2$ | 401 | 77 | 6.2 | 21.3 | 1.1 | 93.8(33.2) | 1.6 | 0.5 | 1.0 | 1.3 | 0.1 | 0.0 |
| 1 $MoO_3/SiO_2$ | 449 | 79 | 1.8 | 25.5 | 0.3 | 98.2(27.9) | 0.5 | 0.1 | 0.3 | 0.5 | — | — |
| 2 $TiO_2/MoO_3/SiO_2$ | 447 | 80 | 3.3 | 19.7 | 0.6 | 96.7(34.9) | 1.1 | 0.2 | 0.5 | 0.7 | 0.0 | — |

*gm 1-hexene/gm catalyst/hr (feed rate)

Inspection of the table above shows that the $TiO_2/MoO_3/SiO_2$ catalyst causes higher conversion of 1-hexene than does the $MoO_3/SiO_2$ catalyst. It also results in lower selectivity to $C_{10}$ olefins, normally the major disproportionation product. However, the $TiO_2/MoO_3/SiO_2$ catalyst also contains greater olefin isomerization as shown in the higher concentrations of $C_5$–$C_{12}$ olefin products and 2-hexene. The $C_5$–$C_{12}$ olefin products result from the disproportionation of isomerized hexenes and other product olefins. While 3-hexene is most likely present, it could not be separated from the 1-hexene in this analysis. The amount of 3-hexene should increase as the 2-hexene increases. Thus, the improved isomerization is probably even greater than indicated in the table.

I claim:

1. An activated composition suitable for the disproportionation and isomerization of olefins consisting essentially of silica and molybdenum oxide promoted with an effective promoting amount of a titaniferous agent.

2. A composition according to claim 1 wherein said catalytic amount of molybdenum oxide is in the range of about 0.1 to about 30 percent by weight of the combined weights of molybdenum and silica.

3. A composition according to claim 2 wherein the titaniferous agent is precipitated on the surface of the silica-molybdenum oxide and is employed in an amount in the range of about 0.1 to about 20 weight percent of the titanium component calculated as titanium dioxide based on the weight of molybdenum oxide-silica combination.

4. An activated catalyst suitable for the disproportionation and isomerization of olefins consisting essentially of silica, about 1 to about 20 weight percent molybdenum oxide, and about 0.1 to about 20 weight percent of a titanium component calculated as titanium dioxide, said amounts being based on the combined weights of molybdenum oxide and silica.

5. A composition according to claim 4 wherein said titaniferous agent is titanium citrate.

6. A process for preparing a catalyst according to claim 1 which is active for the disproportionation and isomerization of olefins comprising admixing a catalytically effective amount of molybdenum and a silica support with a promoting amount of a titaniferous agent and subjecting same to calcination and, optionally, reducing conditions suitable for converting said titaniferous agent to the oxide and promote the activity of molybdenum oxide and silica for the disproportionation and isomerization of olefins.

7. A process according to claim 5 wherein said titaniferous agent is added in solution to silica containing a molybdenum compound and the resulting composition is heated to an elevated temperature and under calcination conditions and, optionally, then followed by reducing conditions sufficient to activate the catalyst.

8. A process according to claim 7 wherein said catalytic amount of molybdenum oxide is in the range of about 0.1 to about 30 percent of the combined weights of molybdenum oxide and silica.

9. A process according to claim 8 wherein the titaniferous agent is employed in an amount in the range of about 0.1 to about 20 weight percent of the titanium component calculated as titanium dioxide based on the weight of molybdenum oxide-silica combination.

10. A process according to claim 9 wherein said titaniferous agent is bis(triethanolamine)titanium diisopropoxide.

11. A process according to claim 7 wherein said calcination and reducing treatments are carried out at about the same elevated temperature.

* * * * *